(12) United States Patent
Legrand et al.

(10) Patent No.: US 7,066,965 B2
(45) Date of Patent: Jun. 27, 2006

(54) BLEACHING COMPOSITION FOR KERATINOUS FIBERS COMPRISING AN ASSOCIATE POLYURETHANE

(75) Inventors: Frédéric Legrand, Courbevoie (FR); Roland De La Mettrie, Le Vésinet (FR)

(73) Assignee: L'Oreal S.A., Paris (FR)

( * ) Notice: Subject to any disclaimer, the term of this patent is extended or adjusted under 35 U.S.C. 154(b) by 70 days.

(21) Appl. No.: 10/415,953

(22) PCT Filed: Nov. 6, 2001

(86) PCT No.: PCT/FR01/03429

§ 371 (c)(1),
(2), (4) Date: May 7, 2003

(87) PCT Pub. No.: WO02/38117

PCT Pub. Date: May 16, 2002

(65) Prior Publication Data

US 2004/0034947 A1 Feb. 26, 2004

(30) Foreign Application Priority Data

Nov. 8, 2000 (FR) .................................. 00 14320

(51) Int. Cl.
*D06L 3/02* (2006.01)

(52) U.S. Cl. ........................ 8/101; 8/107; 8/109; 8/111; 8/540; 8/552; 8/554; 424/70.21; 424/70.27; 424/70.28

(58) Field of Classification Search ................... 8/101, 8/107, 109, 540, 541, 552, 554, 111; 424/70.21, 424/70.27, 70.28
See application file for complete search history.

(56) References Cited

U.S. PATENT DOCUMENTS

| | | | |
|---|---|---|---|
| 2,261,002 A | 10/1941 | Moore | 266/570 |
| 2,271,378 A | 1/1942 | Searle | 167/22 |
| 2,273,780 A | 2/1942 | Dittmar | 260/28 |
| 2,375,853 A | 5/1945 | Kirby et al. | 260/583 |
| 2,388,614 A | 11/1945 | Kirby et al. | 167/22 |
| 2,454,547 A | 11/1948 | Bock et al. | 260/587.6 |
| 2,528,378 A | 10/1950 | Mannheimer | 265/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,472,840 A | 10/1969 | Stone et al. | 260/231 |
| 3,632,559 A | 1/1972 | Matter et al. | 260/78 |
| 3,836,537 A | 9/1974 | Boerwinkle et al. | 260/29.6 |
| 3,874,870 A | 4/1975 | Green et al. | 71/67 |
| 3,879,376 A | 4/1975 | Vanlerberghe et al. | 260/211 R |
| 3,910,862 A | 10/1975 | Barabas et al. | 260/79.3 |
| 3,912,808 A | 10/1975 | Sokol | 424/71 |
| 3,917,817 A | 11/1975 | Vanlerberghe et al. | 424/70 |
| 3,929,990 A | 12/1975 | Green et al. | 424/78 |
| 3,966,904 A | 6/1976 | Green et al. | 424/78 |
| 4,001,432 A | 1/1977 | Green et al. | 424/329 |
| 4,003,699 A | 1/1977 | Rose et al. | 8/10.2 |
| 4,005,193 A | 1/1977 | Green et al. | 424/168 |
| 4,013,787 A | 3/1977 | Varlerberghe et al. | 424/70 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 260/567.6 |
| 4,027,008 A | 5/1977 | Sokol | 424/62 |
| 4,027,020 A | 5/1977 | Green et al. | 424/248.56 |
| 4,031,025 A | 6/1977 | Vanlerberghe et al. | 252/180 |
| 4,031,307 A | 6/1977 | DeMartino et al. | 536/114 |
| 4,131,576 A | 12/1978 | Iovine et al. | 260/12.4 |
| 4,157,388 A | 6/1979 | Christiansen | 624/70 |
| 4,165,367 A | 8/1979 | Chakrabarti | 424/47 |
| 4,172,887 A | 10/1979 | Vanlerberghe et al. | 424/70 |
| 4,189,468 A | 2/1980 | Vanlerberghe et al. | 424/70 |
| 4,197,865 A | 4/1980 | Jacquet et al. | 132/7 |
| 4,217,914 A | 8/1980 | Jacquet et al. | 132/7 |
| 4,223,009 A | 9/1980 | Chakrabarti | 424/47 |
| 4,240,450 A | 12/1980 | Grollier et al. | 132/7 |
| 4,277,581 A | 7/1981 | Vanlerberghe et al. | 525/420 |
| 4,348,202 A | 9/1982 | Grollier et al. | 8/406 |
| 4,349,532 A | 9/1982 | Vanlerberghe et al. | 424/47 |
| 4,381,919 A | 5/1983 | Jacquet et al. | 8/405 |
| 4,422,853 A | 12/1983 | Jacquet et al. | 8/406 |
| 4,445,521 A | 5/1984 | Grollier et al. | 132/7 |
| 4,579,732 A | 4/1986 | Grollier et al. | 424/71 |
| 4,591,610 A | 5/1986 | Grollier | 524/55 |
| 4,608,250 A | 8/1986 | Jacquet et al. | 424/71 |
| 4,702,906 A | 10/1987 | Jacquet et al. | 424/70 |
| 4,719,099 A | 1/1988 | Grollier et al. | 424/47 |
| 4,719,282 A | 1/1988 | Nadolsky et al. | 528/310 |

(Continued)

FOREIGN PATENT DOCUMENTS

DE 23 59 399 6/1975

(Continued)

OTHER PUBLICATIONS

English Language DERWENT Abstract of DE 195 43 988.

(Continued)

*Primary Examiner*—Eisa Elhilo
(74) *Attorney, Agent, or Firm*—Finnegan, Henderson, Farabow, Garrett & Dunner LLP

(57) ABSTRACT

The invention concerns bleaching composition for keratinous fibres, in particular human keratinous fibres and more particularly hair, comprising, in a medium suitable for bleaching, at least an oxidising agent and furthermore at least a cationic associative polyurethane. The invention also concerns the bleaching method and devices using said composition.

63 Claims, No Drawings

U.S. PATENT DOCUMENTS

| | | | | |
|---|---|---|---|---|
| 4,761,273 | A | 8/1988 | Grollier et al. | 424/47 |
| 4,777,040 | A | 10/1988 | Grollier et al. | 424/71 |
| 4,803,221 | A | 2/1989 | Bair | 514/510 |
| 4,839,166 | A | 6/1989 | Grollier et al. | 424/71 |
| 4,948,579 | A | 8/1990 | Jacquet et al. | 424/72 |
| 4,970,066 | A | 11/1990 | Grollier et al. | 424/62 |
| 4,996,059 | A | 2/1991 | Grollier et al. | 424/71 |
| 5,009,880 | A | 4/1991 | Grollier et al. | 424/47 |
| 5,057,311 | A | 10/1991 | Kamegai et al. | 424/70 |
| 5,061,289 | A | 10/1991 | Clausen et al. | 8/405 |
| 5,089,252 | A | 2/1992 | Grollier et al. | 424/47 |
| 5,139,037 | A | 8/1992 | Grollier et al. | 132/203 |
| 5,196,189 | A | 3/1993 | Jacquet et al. | 424/72 |
| 5,380,340 | A | 1/1995 | Neunhoeffer et al. | 8/409 |
| 5,478,562 | A | 12/1995 | Cauwet et al. | 424/401 |
| 5,534,267 | A | 7/1996 | Neunhoeffer et al. | 424/701 |
| 5,643,581 | A | 7/1997 | Mougin et al. | 424/401 |
| 5,650,159 | A | 7/1997 | Lion et al. | 424/401 |
| 5,663,366 | A | 9/1997 | Neunhoeffer et al. | 548/371.4 |
| 5,708,151 | A | 1/1998 | Mockli | 534/608 |
| 5,766,576 | A | 6/1998 | Löwe et al. | 424/62 |
| 5,807,957 | A | 9/1998 | Samour et al. | 528/49 |
| 5,876,463 | A | 3/1999 | Garcia et al. | 8/405 |
| 5,888,252 | A | 3/1999 | Möckli | 8/426 |
| 5,958,392 | A | 9/1999 | Grollier et al. | 424/70.17 |
| 6,068,835 | A * | 5/2000 | Franzke et al. | 424/70.11 |
| 6,099,592 | A | 8/2000 | Vidal et al. | 8/409 |
| 6,099,593 | A | 8/2000 | Terranova et al. | 8/409 |
| 6,251,145 | B1 * | 6/2001 | De La Mettrie et al. | 8/407 |
| 6,260,556 | B1 | 7/2001 | Legrand et al. | 132/208 |
| 6,284,003 | B1 | 9/2001 | Rose et al. | 8/412 |
| 6,335,003 | B1 * | 1/2002 | Kim et al. | 424/70.17 |
| 6,379,401 | B1 | 4/2002 | Legrand et al. | 8/431 |
| 6,395,265 | B1 | 5/2002 | Mougin et al. | 424/70.12 |
| 6,410,004 | B1 | 6/2002 | Kim et al. | 424/70.1 |
| 6,416,770 | B1 | 7/2002 | Leduc et al. | 424/401 |
| 6,524,564 | B1 | 2/2003 | Kim et al. | 424/70.12 |
| 6,641,804 | B1 | 11/2003 | Ohta et al. | 424/70.12 |
| 6,800,276 | B1 | 10/2004 | Kim et al. | 424/70.12 |
| 2003/0124079 | A1 | 7/2003 | Mougin et al. | 424/70.11 |
| 2004/0141943 | A1 | 7/2004 | Mougin et al. | 424/70.17 |

FOREIGN PATENT DOCUMENTS

| | | |
|---|---|---|
| DE | 38 43 892 | 6/1990 |
| DE | 41 33 957 | 4/1993 |
| DE | 195 43 988 | 5/1997 |
| DE | 195 43 989 | 5/1997 |
| EP | 0 080 976 | 6/1983 |
| EP | 0 122 324 | 10/1984 |
| EP | 0 337 354 | 10/1989 |
| EP | 0 714 954 | 6/1996 |
| EP | 0 875 237 | 11/1998 |
| EP | 1 035 144 | 9/2000 |
| EP | 1 036 558 | 9/2000 |
| FR | 1 400 366 | 5/1963 |
| FR | 1 492 597 | 9/1966 |
| FR | 1 583 363 | 9/1968 |
| FR | 2 077 143 | 10/1971 |
| FR | 2 080 759 | 11/1971 |
| FR | 2 137 684 | 12/1972 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 750 048 | 12/1997 |
| FR | 2 773 991 | 7/1999 |
| FR | 2 811 993 | 1/2002 |
| GB | 1021400 | 3/1966 |
| GB | 1026978 | 4/1966 |
| GB | 1153196 | 5/1969 |
| GB | 1331819 | 9/1973 |
| GB | 1347051 | 2/1974 |
| GB | 1479786 | 7/1977 |
| GB | 1546809 | 5/1979 |
| JP | 2-19576 | 7/1988 |
| JP | 55-4384 | 11/1988 |
| JP | 7-89822 | 4/1995 |
| JP | 8-504454 | 5/1996 |
| JP | 9-110659 | 4/1997 |
| JP | 10-259115 | 9/1998 |
| JP | 10-509742 | 9/1998 |
| JP | 10-316546 | 12/1998 |
| JP | 2000-239134 | 9/2000 |
| JP | 2000-256141 | 9/2000 |
| JP | 2000-309518 | 11/2000 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 98/28355 | 7/1998 |
| WO | WO 99/17727 * | 4/1999 |
| WO | WO 99/36047 | 7/1999 |
| WO | WO 00/12588 | 3/2000 |

OTHER PUBLICATIONS

English Language DERWENT Abstract of DE 195 43 989.
English Language DERWENT Abstract of DE 38 43 892.
English Language DERWENT Abstract of DE 41 33 957.
English Language DERWENT Abstract of EP 0 080 976.
English Language DERWENT Abstract of EP 0 714 954.
English Language DERWENT Abstract of EP 1 035 144.
English Language DERWENT Abstract of FR 2 190 406.
English Language DERWENT Abstract of FR 2 368 508.
English Language DERWENT Abstract of JP 2000-239134.
English Language DERWENT Abstract of JP 2000-309518.
English Language DERWENT Abstract of JP 2-19576.
Abstract of JP 9-110659 (represented by the DERWENT abstract of related patent DE 195 39 264).
English Language DERWENT Abstract of JP 10-259115.
English Language DERWENT Abstract of WO 00/12588.
International Search Report dated Mar. 26, 2002 in PCT/FR 01/03427 (corresponding to U.S. Appl. No. 10/415,954).
International Search Report dated Mar. 26, 2002 in PCT/FR 01/03428 (corresponding to U.S. Appl. No. 10/415,952).
International Search Report dated Mar. 4, 2002 in PCT/FR 01/03429 (corresponding to the present application).
International Search Report dated Mar. 4, 2002 in PCT/FR 01/03430 (corresponding to U.S. Appl. No. 10/415,937).
Notice of Rejection dated Mar. 22, 2005 in Japanese Patent Application No. 2002-540705 (Japanese counterpart to U.S. Appl. No. 10/415,954).
Notice of Rejection dated Mar. 22, 2005 in Japanese Patent Application No. 2002-540706 (Japanese counterpart to U.S. Appl. No. 10/415,952).

Notice of Rejection dated Mar. 22, 2005 in Japanese Patent Application No. 2002-540707 (Japanese counterpart to the present application).

Notice of Rejection dated Mar. 22, 2005 in Japanese Patent Application Number 2002-540708 (Japanese counterpart to U.S Appl. No. 10/415,937).

Porter, M.R. "Handbook of Surfactants," Blackie & Son, LTD., pp. 116-178 (1991).

Translation of JP 2000-256141.

Translation of JP 10-259115.

Office Action in Co-pending U.S. Appl. No. 10/415,952 dated Nov. 3, 2004 (Examiner Elhilo).

Final Office Action in Co-pending U.S. Appl. No. 10/415,952 dated May 23, 2005 (Examiner Elhilo).

Office Action in Co-pending U.S. Appl. No. 10/415,937 dated Nov. 3, 2004 (Examiner Elhilo).

Final Office Action in Co-pending U.S. Appl. No. 10/415,937 dated May 23, 2005 (Examiner Elhilo).

Office Action in Co-pending U.S. Appl. No. 10/415,954 dated Nov. 4, 2004 (Examiner Elhilo).

Final Office Action in Co-pending U.S. Appl. No. 10/415,954 dated May 12, 2005 (Examiner Elhilo).

Co-pending U.S. Appl. No. 10/415,952, Title: Oxidation Dye Composition for Keratin Fibers Comprising a Cationic Associative Polyurethane Inventors: Francois Cottard et al. U.S. Filing Date: May 7, 2003.

Co-pending U.S. Appl. No. 10/415,937, Title: Composition for Bleaching or Permanently Reshaping Keratin Fibers, Comprising a Cationic Associative Polyurethane Inventors: Frederic Legrand et al. U.S. Filing Date: May 7, 2003.

Co-pending U.S. Appl. No. 10/415,954, Title: Direct Dye Composition for Keratin Fibers Comprising a Cationic Associative Polyurethane Inventors: Francois Cottard et al. U.S. Filing Date: May 7, 2003.

* cited by examiner

BLEACHING COMPOSITION FOR KERATINOUS FIBERS COMPRISING AN ASSOCIATE POLYURETHANE

The present invention relates to a composition for bleaching keratin fibers, in particular human keratin fibers and more particularly the hair, comprising at least one oxidizing agent and at least one cationic associative polyurethane.

It is known practice to bleach keratin fibers, and in particular human hair, with bleaching compositions containing one or more oxidizing agents. Among the oxidizing agents conventionally used, mention may be made of hydrogen peroxide or of compounds capable of producing hydrogen peroxide by hydrolysis, such as urea peroxide or persalts, for instance perborates, percarbonates and persulfates, hydrogen peroxide and persulfates being particularly preferred.

Said bleaching compositions are mainly in the form of anhydrous products (powders or creams) containing alkaline compounds (amines and alkaline silicates), and a peroxygenated agent such as ammonium or alkali metal persulfates, perborates or percarbonates, which is diluted at the time of use with an aqueous hydrogen peroxide composition.

Bleaching compositions may also result from mixing, at the time of use, the anhydrous powder of peroxygenated reagent with an aqueous composition containing alkaline compounds and another aqueous composition containing the hydrogen peroxide.

Bleaching compositions are also in the form of ready-to-use thickened aqueous hydrogen peroxide compositions.

For the purposes of the invention, the expression "ready-to-use composition" means the composition intended to be applied, without further modification, to the keratin fibers, i.e. it may be stored in a modified form before use or may result from the extemporaneous mixing of two or more compositions To localize the bleaching product on application to the hair so that it does not run down the face or beyond the areas which it is proposed to bleach, use has been made hitherto of conventional thickeners such as crosslinked polyacrylic acid, hydroxyethylcelluloses, certain polyurethanes, waxes and, in the case of aqueous bleaching compositions, mixtures of nonionic surfactants with an HLB (Hydrophilic-Lipophilic Balance) value, which, when suitably chosen, give rise to a gelling effect when they are diluted with water and/or surfactants.

However, the Applicant has found that the thickening systems mentioned above do not make it possible to obtain sufficiently intense and homogenous bleachings and leave the hair rough.

Moreover, the Applicant has also found that ready-to-use bleaching compositions containing the oxidizing agent(s) and also the thickener systems of the prior art do not allow a sufficiently precise application without running or falls in viscosity over time.

After considerable research conducted in this matter, the Applicant has now discovered that it is possible to obtain ready-to-use bleaching compositions that do not run and thus remain satisfactorily localized at the point of application, and which produce powerful and homogeneous bleaching results while at the same time leaving the hair less coarse, if an effective amount of a cationic associative polyurethane is introduced into the composition.

These discoveries form the basis of the present invention.

One subject of the present invention is thus a ready-to-use composition for bleaching keratin fibers, in particular for human keratin fibers and more particularly the hair, comprising, in a medium that is suitable for bleaching, at least one oxidizing agent, which is characterized in that it also comprises at least one cationic associative polyurethane.

According to the invention, said composition is anhydrous or aqueous.

When the ready-to-use composition according to the invention results from the extemporaneous mixing of several compositions, the cationic associative polyurethane may be present in one or more or in all of the mixed compositions.

Accordingly, the cationic associative polyurethane may be present in an anhydrous composition in the form of a powder, preferably a pulverulent powder, or in the form of a cream and/or in one or more aqueous compositions.

Preferably, according to the invention, the cationic associative polyurethane is present in at least one aqueous composition that is mixed at the time of use with an anhydrous composition in powder or cream form containing at least one oxidizing agent.

Even more preferably, one of these aqueous compositions mixed with the anhydrous composition contains hydrogen peroxide.

The invention is also directed toward a process for bleaching keratin fibers, in particular for human keratin fibers and more particularly the hair, using the ready-to-use bleaching composition as described according to the invention.

The invention is also directed toward packaging bleaching devices or "kits" for human keratin fibers, and more particularly the hair, comprising such a ready-to-use composition.

Thus, a two-compartment device comprises a first compartment comprising at least one anhydrous powder or cream or an aqueous composition, and a second compartment comprising an aqueous composition, at least one of the two compartments comprising at least one oxidizing agent and at least one of the two compartments comprising at least one cationic associative polyurethane.

Another multi-compartment "kit" may consist of a first compartment comprising an anhydrous powder or cream and two other compartments each comprising an aqueous composition, at least one of the three compartments comprising at least one oxidizing agent and at least one of the three compartments comprising at least one cationic associative polyurethane.

However, other characteristics, aspects, subjects and advantages of the invention will emerge even more clearly on reading the description and the examples that follow.

Associative polymers are polymers whose molecules are capable, in the formulation medium, of combining with each other or with the molecules of other compounds.

One special case of associative polymers is amphiphilic polymers, i.e. polymers comprising one or more hydrophilic portions which make them water-soluble, and one or more hydrophobic zones (comprising at least one fatty chain) via which the polymers interact and assemble together or with other molecules.

Cationic Associative Polyurethanes

The cationic associative polyurethanes according to the present invention are chosen more particularly from water-soluble or water-dispersible cationic associative amphiphilic polyurethanes.

The term "water-soluble" regarding the associative polyurethanes of the present invention means that these polymers have a solubility in water at room temperature of at least 1% by weight, i.e. up to this concentration, no precipitate is visible to the naked eye, and the solution is totally clear and uniform.

The term "water-dispersible" polyurethanes means polymers which, when suspended in water, spontaneously form globules that have a mean size, measured by light scattering on a Coulter machine, of between 5 nm and 600 nm and in particular between 5 nm and 500 nm.

The family of cationic associative polyurethanes according to the invention was described by the Applicant in French patent application No 00/09609; it may be represented by the general formula (Ia) below:

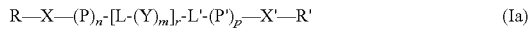

in which:
- R and R', which may be identical or different, represent a hydrophobic group or a hydrogen atom;
- X and X', which may be identical or different, represent a group comprising an amine function optionally bearing a hydrophobic group, or alternatively a group L";
- L, L' and L", which may be identical or different, represent a group derived from a diisocyanate;
- P and P', which may be identical or different, represent a group comprising an amine function optionally bearing a hydrophobic group;
- Y represents a hydrophilic group;
- r is an integer between 1 and 100, preferably between 1 and 50 and in particular between 1 and 25,
- n, m and p each range, independently of each other, from 0 to 1000;
- the molecule containing at least one protonated or quaternized amine function and at least one hydrophobic group.

In one preferred embodiment of the polyurethanes of the present invention, the only hydrophobic groups are the groups R and R' at the chain ends.

One preferred family of cationic associative polyurethanes is the one corresponding to formula (Ia) described above and in which:
- R and R' both independently represent a hydrophobic group,
- X and X' each represent a group L",
- n and p are between 1 and 1000, and
- L, L', L", P, P', Y and m have the meaning given above.

Another preferred family of cationic associative polyurethanes is the one corresponding to formula (Ia) above in which:
- R and R' both independently represent a hydrophobic group, X and X' each represent a group L", n and p are 0, and L, L', L", Y and m have the meaning given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to formula (Ia) above in which:
- R and R' both independently represent a hydrophobic group,
- X and X' both independently represent a group comprising a quaternary amine,
- n and p are zero, and
- L, L', Y and m have the meaning given above.

The number-average molecular mass of the cationic associative polyurethanes is preferably between 400 and 500 000, in particular between 1000 and 400 000 and ideally between 1000 and 300 000.

The expression "hydrophobic group" means a radical or polymer containing a saturated or unsaturated, linear or branched hydrocarbon-based chain, which may contain one or more hetero atoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer such as, for example, polybutadiene.

When X and/or X' denote(s) a group comprising a tertiary or quaternary amine, X and/or X' may represent one of the following formulae:

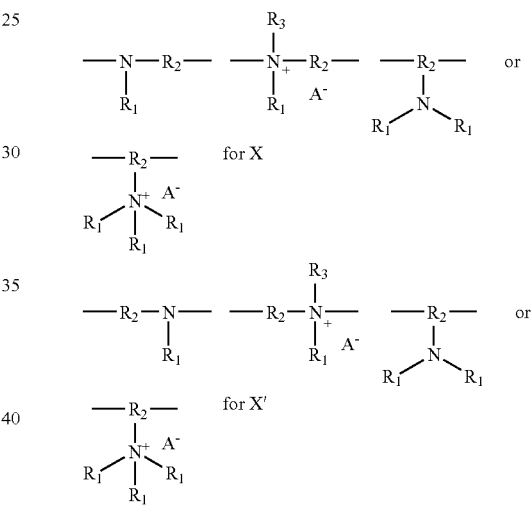

in which:
- $R_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;
- $R_1$ and $R_3$, which may be identical or different, denote a linear or branched $C_1$–$C_{30}$ alkyl or alkenyl radical or an aryl radical, at least one of the carbon atoms possibly being replaced with a hetero atom chosen from N, S, O and P;
- $A^-$ is a physiologically acceptable counterion.

The groups L, L' and L" represent a group of formula:

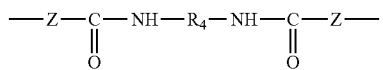

in which:
- Z represents —O—, —S— or —NH—; and
- $R_4$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P.

The groups P and P' comprising an amine function may represent at least one of the following formulae:

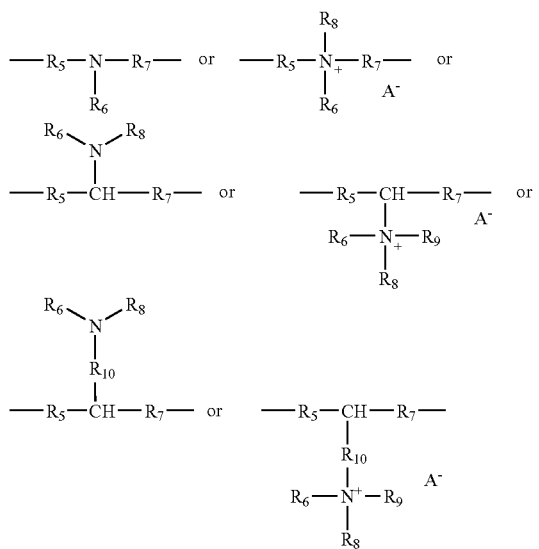

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group possibly containing one or more hetero atoms chosen from N, O, S and P; and $A^-$ is a physiologically acceptable counterion.

As regards the meaning of Y, the term "hydrophilic group" means a polymeric or nonpolymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The cationic associative polyurethanes of formula (Ia) according to the invention are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The term "polyurethanes" in the present invention encompasses these three types of polymer, namely polyurethanes per se, polyureas and polythioureas, and also copolymers thereof.

A first type of compound involved in the preparation of the polyurethane of formula (Ia) is a compound comprising at least one unit containing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used.

As mentioned above, this compound may comprise more than one unit containing an amine function. In this case, it is a polymer bearing a repetition of the unit containing an amine function.

Compounds of this type may be represented by one of the following formulae:

$$HZ-(P)_n-ZH$$

or $$HZ-(P')_p-ZH$$

in which Z, P, P', n and p are as defined above.

Examples of compounds containing an amine function that may be mentioned include N-methyldiethanolamine, N-tert-butyldiethanolamine and N-sulfoethyldiethanolamine.

The second compound involved in the preparation of the polyurethane of formula (Ia) is a diisocyanate corresponding to the formula:

$$O=C=N-R_4-N=C=O$$

in which $R_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound consists of a hydrophobic group and of a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymeric chain, it may be, for example, [lacuna]-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are, however, preferred.

Said cationic associative polyurethanes are water-soluble or water-dispersible.

The cationic associative polyurethane(s) according to the invention is (are) preferably used in an amount that may range from about 0.01% to 10% by weight relative to the total weight of the ready-to-use dye composition. More preferably, this amount ranges from about 0.1% to 5% by weight.

The oxidizing agents that may be used according to the invention are preferably chosen from hydrogen peroxide and compounds that release hydrogen peroxide by hydrolysis, such as urea peroxide and persalts.

Persalts that may be used according to the invention include alkali metal or alkaline-earth metal persulfates and perborates and in particular sodium persulfate or potassium persulfate.

Other oxidizing agents that may be mentioned include chlorites.

An enzymatic system that generates oxidizing species and in particular hydrogen peroxide may also be used. Examples of such enzymatic systems that may be mentioned include two-electron oxidoreductases combined with their donor in the presence of air and more particularly the uricase/uric acid/air system.

Organic peroxides may also be used.

The hydrogen peroxide concentration of the ready-to-usecompositions may range from 2 to 40 volumes. That of the other compounds including, in particular, the compounds capable of forming hydrogen peroxide by hydrolysis, may range from 0.1% to 25% by weight approximately relative to the total weight of the composition.

In addition to the oxidizing agents defined above, the composition according to the invention may also comprise direct dyes. These direct dyes may be chosen especially from neutral, acidic or cationic nitro, azo and anthraquinone dyes.

More particularly, the compositions according to the invention may also comprise at least one amphoteric or cationic substantive polymer other than the cationic associative polyurethanes of the invention.

Cationic Polymers

For the purposes of the present invention, the term "cationic polymer" denotes any polymer containing cationic groups and/or groups that may be ionized into cationic groups.

The cationic polymers that may be used in accordance with the present invention may be chosen from all those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type.

These are known products. They are described in particular in French patents Nos 2 505 348 and 2 542 997. Among said polymers, mention may be made of:

(1) homopolymers or copolymers derived from acrylic or methacrylic esters or amides and comprising at least one of the units of formula (I), (II), (III) or (IV) below:

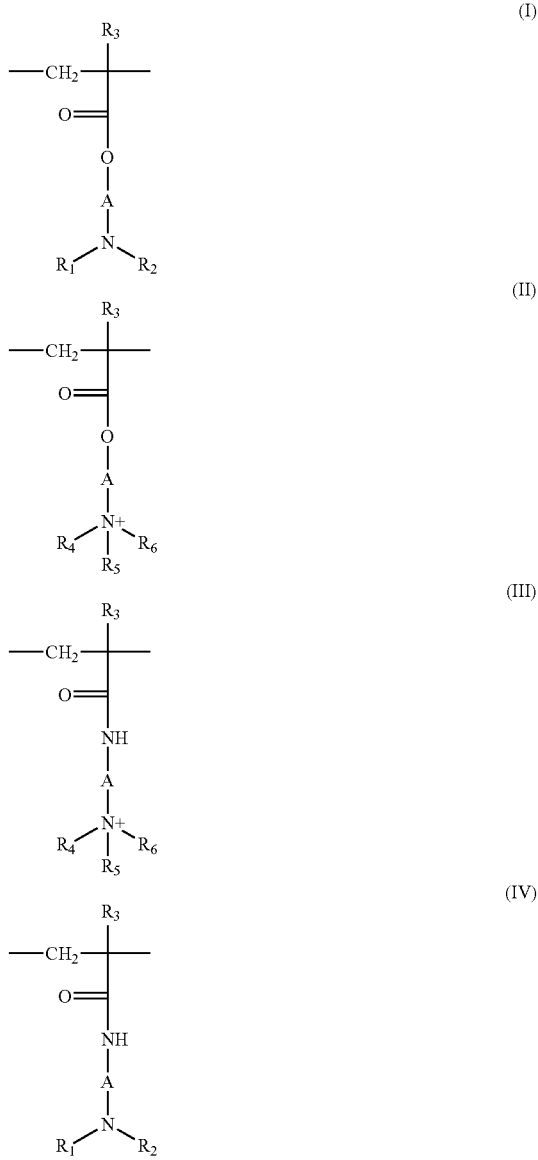

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl; X denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or nonquaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropylmethacrylamide copolymers, such as the product sold under the name "Gafquat HS 100" by the company ISP.

(2) The cellulose ether derivatives containing quaternary ammonium groups, described in French patent 1 492 597, and in particular polymers sold under the names "JR" (JR 400, JR 125 and JR 30M) or "LR" (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble quaternary ammonium monomer, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

(V)

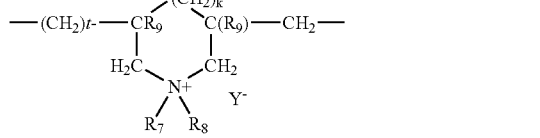

(VI)

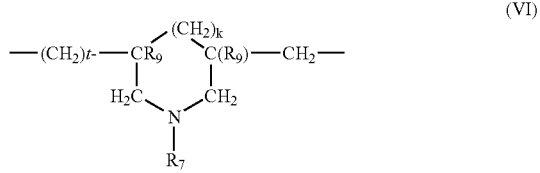

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 22 carbon atoms, a hydroxyalkyl group in which the alkyl group preferably has 1 to 5 carbon atoms, a lower $C_1$–$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Calgon (and its homologs of low weight-average molecular mass) and the copolymers of diallyldimethylammonium chloride and of acrylamide, sold under the name "Merquat 550".

(10) The quaternary diammonium polymer containing repeating units corresponding to the formula:

(VII)

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O—Z—O—, where Z denotes a linear or branched hydrocarbon-based radical or a group corresponding to one of the following formulae:

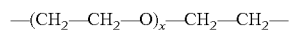

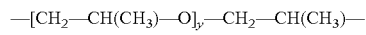

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

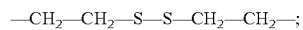

d) a ureylene group of formula: —NH—CO—NH—.

Preferably, $X^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to formula (VIII) below:

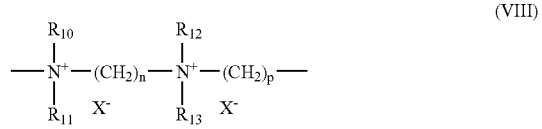

(VIII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

(11) Polyquaternary ammonium polymers consisting of repeating units of formula (IX):

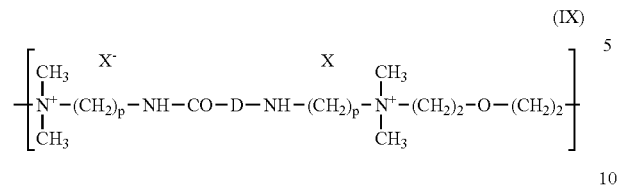

in which p denotes an integer ranging from 1 to 6 approximately, D may be nothing or may represent a group —$(CH_2)_r$—CO— in which r denotes a number equal to 4 or 7, $X^-$ is an anion.

Such polymers may be prepared according to the processes described in U.S. Pat. Nos. 4,157,388, 4,702,906 and 4,719,282. They are described in particular in patent application EP-A-122 324.

Among these products, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as, for example, the products sold under the names Luviquat FC 905, FC 550 and FC 370 by the company BASF.

(13) Polyamines such as Polyquart H sold by Henkel, which is given under the reference name "Polyethylene glycol (15) tallow polyamine" in the CTFA dictionary.

(14) Crosslinked methacryloyloxy($C_1$–$C_4$)alkyltri($C_1$–$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (1), (9), (10), (11) and (14) and even more preferably the polymers consisting of repeating units of formulae (W) and (U) below:

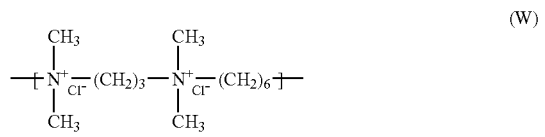

and in particular those whose molecular weight, determined by gel permeation chromatography, is between 9500 and 9900;

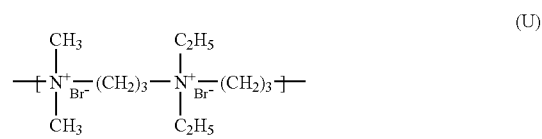

and in particular those whose molecular weight, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers that may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/ acrylamidopropyltrimethylammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:
a) at least one monomer chosen from acrylamides and methacrylamides substituted on the nitrogen with an alkyl radical,
b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is Octylacrylamide/acrylates/butylaminoethyl methacrylate copolymer such as the products sold under the name Amphomer or Lovocryl 47 by the company National Starch are particularly used.

(3) Polyamino amides that are crosslinked and alkylated partially or totally derived from polyamino amides of general formula:

(X)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

(XI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) Polymers containing zwitterionic units of formula:

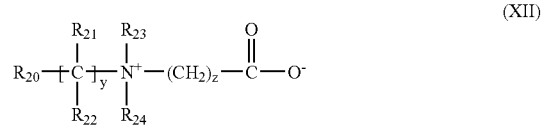

(XII)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethyl carboxymethylammonio ethyl methacrylate such as the product sold under the name Diaformer Z301 by the company Sandoz.

(5) Polymers derived from chitosan, described especially in French patent No 2 137 684 or U.S. Pat. No. 3,879,376, containing monomer units corresponding to formulae (XIII), (XIV) and (XV) below connected in their chain:

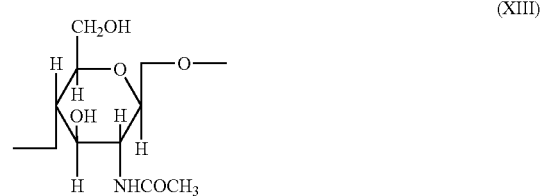

(XIII)

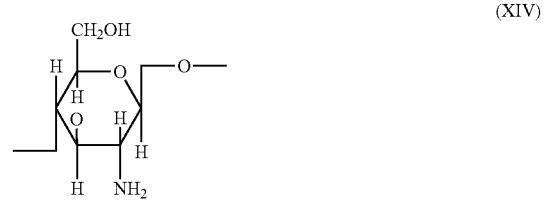

(XIV)

-continued

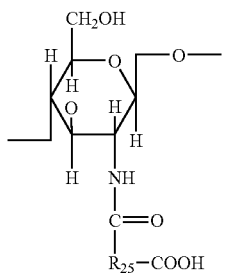

(XV)

the unit (XIII) being present in proportions of between 0 and 30%, the unit (XIV) in proportions of between 5 and 50% and the unit (XV) in proportions of between 30 and 90%, it being understood that, in this unit (XV), $R_{25}$ represents a radical of formula:

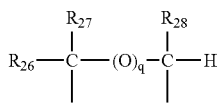

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XI) as described, for example, in French patent 1 400 366:

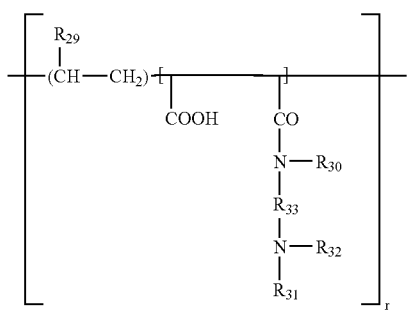

(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: $—R_{33}—N(R_{31})_2$, $R_{33}$ representing a $—CH_2—CH_2—$, $—CH_2—CH_2—CH_2—$ or $—CH_2—CH(CH_3)—$ group, $R_{31}$ having the meanings mentioned above, as well as the higher homologs of these radicals and containing up to 6 carbon atoms, r is such that the molecular weight is between 500 and 6 000 000 and preferably between 1000 and 1 000 000.

(8) Amphoteric polymers of the type -D-X-D-X- chosen from:

a) polymers obtained by the action of chloroacetic acid or sodium chloroacetate on compounds containing at least one unit of formula:

-D-X-D-X-D- (XVII)

where D denotes a radical

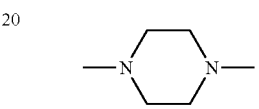

X denotes the symbol E or E', E or E', which may be identical or different, denotes a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X- (XVIII)

where D denotes a radical

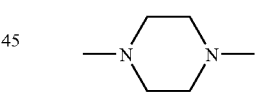

and X denotes the symbol E or E' and at least once E';

E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) may represent from 0.01% to 10% by weight, preferably from 0.05% to 5% by weight and even more preferably from 0.1% to 3% by weight relative to the total weight of the composition.

The compositions of the invention preferably comprise one or more surfactants.

The surfactant(s) can be chosen without preference, alone or as mixtures, from anionic, amphoteric, nonionic, zwitterionic and cationic surfactants.

The surfactants that are suitable for carrying out the present invention are, in particular, the following:

(i) Anionic Surfactant(s):

As examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$–$C_{24}$) alkyl sulfosuccinates, ($C_6$–$C_{24}$) alkyl ether sulfosuccinates, ($C_6$–$C_{24}$) alkylamide sulfosuccinates; ($C_6$–$C_{24}$) alkyl sulfoacetates; ($C_6$–$C_{24}$) acyl sarcosinates and ($C_6$–$C_{24}$) acyl glutamates. It is also possible to use the carboxylic esters of ($C_6$–$C_{24}$) alkylpolyglycosides, such as alkylglucoslde citrates, alkylpolyglycoside tartrates and alkylpolyglycoside sulfosuccinates, alkylsulfosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, in particular those containing from 2 to 50 alkylene oxide, in particular ethylene oxide, groups, and mixtures thereof can also be used.

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (nonlimiting list) polyethoxylated or polypropoxylated alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (nonlimiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of ($C_8$–$C_{20}$)alkylbetaines, sulfobetaines, ($C_8$–$C_{20}$)alkylamido ($C_1$–$C_6$)alkylbetaines or ($C_8$–$C_{20}$)alkylamido($C_1$–$C_6$)alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures:

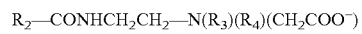

in which:

$R_2$ denotes an alkyl radical of an acid $R_2$—COOH present in hydrolyzed coconut oil, a heptyl, nonyl or undecyl radical, $R_3$ denotes a β-hydroxyethyl group and $R_4$ denotes a carboxymethyl group;

and

in which:

B represents —$CH_2CH_2OX'$, C represents —$(CH_2)_z$—Y', with z=1 or 2,

X' denotes a —$CH_2CH_2$—COOH group or a hydrogen atom,

Y' denotes —COOH or a —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caproamphodipropionate, lauroamphodipropionic acid and cocoamphodipropionic acid.

By way of example, mention may be made of the cocoamphodiacetate sold under the trade name Miranol® C2M Concentrate by the company Rhodia Chimie.

(iv) Cationic Surfactants:

Among the cationic surfactants that may be mentioned in particular (nonlimiting list) are: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can range from 0.01% to 40% and preferably from 0.5% to 30% relative to the total weight of the composition.

The compositions according to the invention can also comprise other agents for adjusting the rheology, such as cellulose-based thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), synthetic thickeners such as crosslinked acrylic acid or acrylamidopropanesulfonic acid homopolymers and ionic or nonionic associative polymers such as the polymers sold under the names Pemulen TR1 or TR2 by the company Goodrich, Salcare SC90 by the company Allied Colloids, Aculyn 22, 28, 33, 44 or 46 by the company Rohm & Haas, and Elfacos T210 and T212 by the company Akzo.

These additional thickeners can represent from 0.05% to 10% by weight relative to the total weight of the composition.

The compositions according to the invention also advantageously comprise at least one basifying agent in amounts ranging from 0.05% to 30% by weight relative to the total weight of the composition.

Among the basifying agents that may be mentioned, for example, are aqueous ammonia, ammonium chloride, alkali metal or alkaline-earth metal carbonates, alkali metal or alkaline-earth metal silicates, alkali metal or alkaline-earth metal phosphates, alkanolamines such as monoethanolamine, diethanolamine or triethanolamine, and derivatives thereof, sodium hydroxide, potassium hydroxide and the compounds of formula (XIX) below:

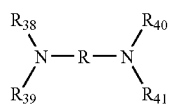

(XIX)

in which R is a propylene residue optionally substituted with a hydroxyl group or a $C_1$–$C_4$ alkyl radical; $R_{38}$, $R_{39}$, $R_{40}$ and $R_{41}$, which may be identical or different, represent a hydrogen atom, a $C_1$–$C_4$ alkyl radical or a $C_1$–$C_4$ hydroxyalkyl radical.

The compositions of the invention may also comprise sequestering agents such as, for example, ethylenediaminetetraacetic acid (EDTA).

When the compositions comprising the oxidizing agent and the cationic associative polyurethane are in anhydrous form (powder or cream), they comprise the main agents and additives mentioned above in the form of essentially anhydrous solids or liquids.

They may also comprise mineral or organic fillers such as silica or clays, binders such as vinylpyrrolidone, oils or waxes, polyalkylene glycols or polyalkylene glycol derivatives, lubricants, for instance polyol stearates or alkali metal or alkaline-earth metal stearates, and also colorants or matting agents, for instance titanium oxides, each of these additives possibly being present at a concentration ranging from 0 to 30% by weight relative to the total weight of the composition.

When the medium containing the oxidizing agent is an aqueous medium, it may optionally contain cosmetically acceptable organic solvents including, more particularly, alcohols such as ethyl alcohol, isopropyl alcohol, benzyl alcohol and phenylethyl alcohol, or glycols or glycol ethers such as, for example, ethylene glycol monomethyl, monoethyl and monobutyl ethers, propylene glycol or its ethers such as, for example, propylene glycol monomethyl ether, butylene glycol, dipropylene glycol, and also diethylene glycol alkyl ethers such as, for example, diethylene glycol monoethyl or monobutyl ether. The solvents may then be present in concentrations of between about 0.5% and 20% and preferably between about 2% and 10% by weight relative to the total weight of the composition.

The bleaching composition according to the invention may also comprise an effective amount of other agents, which are previously known elsewhere in the bleaching of keratin fibers, such as various common adjuvants, for instance volatile or nonvolatile, cyclic or linear or branched, organomodified (especially with amine groups) or non-organomodified silicones, preserving agents, ceramides, plant, mineral or synthetic waxes or oils, acids and in particular AHAs, associative polymers other than those of the invention, and in particular nonionic associative polyurethane polyethers, etc.

Needless to say, persons skilled in the art will take care to select the optional additional compound(s) mentioned above, such that the advantageous properties intrinsically associated with the composition for bleaching keratin fibers according to the invention are not, or are not substantially, adversely affected by the envisaged addition(s).

The pH of the ready-to-use composition is generally between 4 and 12. It is preferably between 7 and 11.5 and even more preferably between 8 and 11.

Preferably, the bleaching process according to the invention consists in applying the ready-to-use bleaching composition to the wet or dry keratin fibers, leaving the composition to act for an action time preferably ranging from 1 to 60 minutes approximately and more preferably from 10 to 45 minutes approximately, rinsing the fibers and then optionally washing them with shampoo, followed by rinsing them again and drying them.

Concrete examples illustrating the invention are given below, without, however, having any limiting nature.

EXAMPLE 1

The ready-to-use aqueous bleaching compositions below were prepared (expressed in grams):

|  | A | B |
|---|---|---|
| 200-volumes hydrogen peroxide | 12 | 12 |
| Stabilizer | qs | qs |
| Polymer 1 | 0.3 AM* |  |
| Polymer 2 |  | 0.3 AM* |
| pH agent | qs pH 4.7 | qs pH 4.7 |
| Water | qs 100 g | 100 g |

AM* = Active Material

Polymer 1 is the following polymer:

$C_{18}H_{37}$—O—CONHR$_4$NHCO—O—$(CH_2)_2$—N$^+$(CH$_3$)(CH$_3$)—$(CH_2)_2$—O—CONHR$_2$NHCO—O—(POE)O—CONHR$_2$NHCO—O—$(CH_2)_2$—N$^+$(CH$_3$)(CH$_3$)—$(CH_2)_2$—O—CONHR$_4$NHCO—OC$_{18}$H$_{37}$ with:

$R_4$=methylenedicyclohexyl counterion: $CH_3SO_4^-$

It is synthesized from the following reagents:

| | |
|---|---|
| $C_{18}H_{37}OH$ | 2 mol |
| Methylenedicyclohexyl diisocyanate | 4 mol |
| Polyethylene glycol | 1 mol |
| N-Methylethanolamine | 2 mol |
| Quaternizing agent $(CH_3)_2SO_4$ | 2 mol |

Polymer 2 is the following polymer:

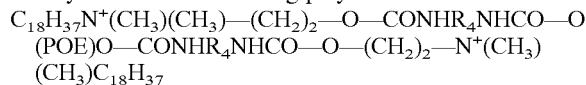

with:

$R_4$=methylenedicyclohexyl counterion: $Cl^-$

It is synthesized from the following reagents:

| | |
|---|---|
| Methylenedicyclohexyl diisocyanate | 2 mol |
| Polyethylene glycol | 1 mol |
| N,N-Dimethylethanolamine | 2 mol |
| Quaternizing agent $C_{18}H_{37}OH$ | 2 mol |

The above bleaching compositions were applied to natural hair and left on the hair for 45 minutes under a hood, and then rinsed out thoroughly with water. Uniform lightening of the hair was obtained.

EXAMPLE 2

The bleaching compositions below were prepared (expressed in grams):

| Anhydrous compositions | A | B |
|---|---|---|
| Potassium persulfate | 35 | 35 |
| Sodium persulfate | 30 | 30 |
| Sodium metasilicate | 14 | 14 |
| Ammonium chloride | 5 | 5 |
| EDTA | 1 | 1 |
| Sodium dioctylsulfosuccinate/sodium benzoate | 1 | 1 |
| Calcium stearate | 1 | 1 |
| Polymer 1 | 3 AM* | |
| Polymer 2 | | 3 AM* |
| Silica | 7 | 7 |

AM* = Active Material 40 g of the above anhydrous compositions were mixed with 80 g of the following aqueous composition:

| Aqueous composition | |
|---|---|
| Cetearyl alcohol/ceteareth 30 | 2.85 |
| Stabilizers | 0.06 |
| Sequestering agent | 0.15 |
| 200-volumes hydrogen peroxide | 9 |
| Phosphoric acid qs | pH 2 |
| Distilled water qs | 100 g |

Ready-to-use bleaching creams were thus obtained, which, when applied and left for 45 minutes under a hood, produced powerful and uniform bleaching of natural dark hair.

The invention claimed is:

1. A ready-to-use composition for bleaching keratin fibers, comprising, in a medium suitable for bleaching, at least one oxidizing agent and at least one cationic associative polyurethane of formula (Ia):

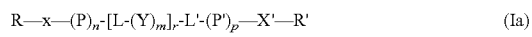

wherein:
R and R', which may be identical or different, are chosen from hydrophobic groups and hydrogen;
X and X', which may be identical or different, are chosen from groups L" and groups comprising at least one amine functional group optionally bearing at least one hydrophobic group;
L, L', and L", which may be identical or different, are chosen from groups derived from diisocyanates;
P and P', which may be identical or different, are chosen from groups comprising at least one amine functional group optionally bearing at least one hydrophobic group;
Y is chosen from hydrophilic groups;
r is an integer ranging from 1 to 100; and
n, m, and p, which may be identical or different, range from 0 to 1000; provided that the at least one cationic associative polyurethane comprises at least one amine functional group chosen from protonated and quaternized amine functional groups, and at least one hydrophobic group.

2. The composition of claim 1, wherein the keratin fibers are human keratin fibers.

3. The composition of claim 2, wherein the human keratin fibers are hair.

4. The composition of claim 1, wherein r is an integer ranging from 1 to 50.

5. The composition of claim 4, wherein r is an integer ranging from 1 to 25.

6. The composition of claim 1, wherein Rand R', which may be identical or different, are chosen from hydrophobic groups;
X and X', which may be identical or different, are chosen from groups L"; and
n and p, which may be identical or different, range from 1 to 1000.

7. The composition of claim 1, wherein R and R', which may be identical or different, are chosen from hydrophobic groups;
X and X', which may be identical or different, are chosen from groups comprising at least one quaternary amine functional group; and
n and p are zero.

8. The composition of claim 1, wherein R and R', which may be identical or different, are chosen from:
radicals and polymers comprising at least one hydrocarbon-based chain chosen from saturated and unsaturated, linear and branched hydrocarbon-based chains, wherein at least one of the carbon atoms of the at least one hydrocarbon-based chain is optionally replaced with a hetero atom chosen from S, N, O, and P; and
radicals and polymers comprising at least one chain chosen from perfluoro and silicone chains.

9. The composition of claim 1, wherein X and X', which may be identical or different, are chosen from groups of the following formulae:

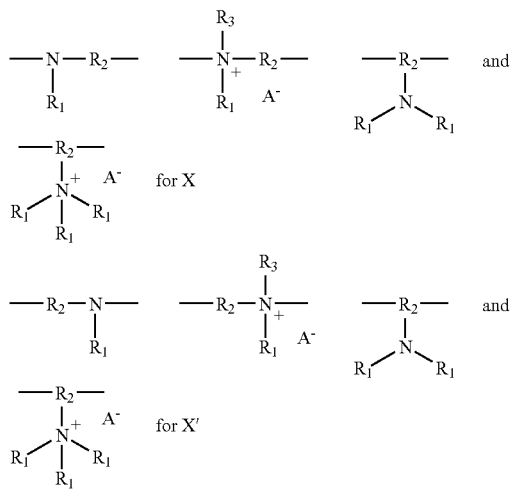

for X for X' wherein:
- $R_2$ is chosen from linear and branched alkylene radicals comprising from 1 to 20 carbon atoms, optionally comprising at least one ring chosen from saturated and unsaturated rings, and arylene radicals, wherein at least one of the carbon atoms of the alkylene radicals, and the arylene radicals is optionally replaced with a hetero atom chosen from N, S, O, and P;
- $R_1$ and $R_3$, which may be identical or different, are chosen from linear and branched $C_1$–$C_{30}$ alkyl and alkenyl radicals and aryl radicals, wherein at least one of the carbon atoms of the alkyl radicals, the alkenyl radicals and the aryl radicals is optionally replaced with a hetero atom chosen from N, S, O, and P; and
- $A^-$ is chosen from physiologically acceptable counterions.

10. The composition of claim 1, wherein the groups L, L', and L", which may be identical or different, are chosen from groups of the following formula:

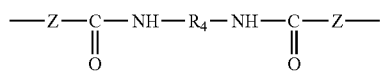

wherein:
- Z is chosen from —O—, —S—, and NH—; and
- $R_4$ is chosen from linear and branched alkylene radicals comprising from 1 to 20 carbon atoms, optionally comprising at least one ring chosen from saturated and unsaturated rings, and arylene radicals, wherein at least one of the carbon atoms of the alkylene radicals and the arylene radicals is optionally replaced with a hetero atom chosen from N, S, O, and P.

11. The composition of claim 1, wherein the groups P and P', which may be identical or different, are chosen from groups of the following formulae:

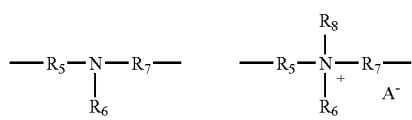

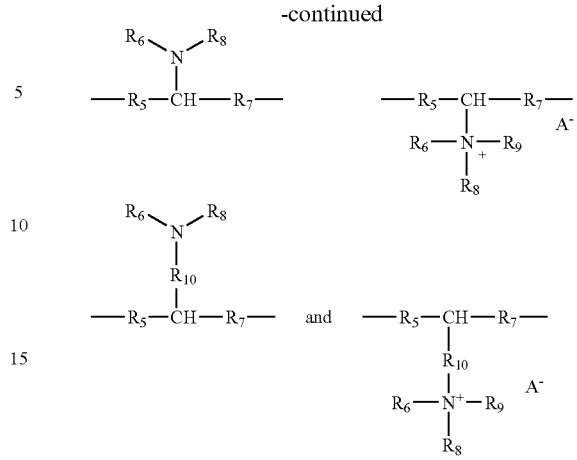

wherein:
- $R_5$ and $R_7$, which may be identical or different, are chosen from linear and branched alkylene radicals comprising from 1 to 20 carbon atoms, optionally comprising at least one ring chosen from saturated and unsaturated rings, and arylene radicals, wherein at least one of the carbon atoms of the alkylene radicals and the arylene radicals is optionally replaced with a hetero atom chosen from N, S, O, and P;
- $R_6$, $R_8$, and $R_9$, which may be identical or different, are chosen from linear and branched $C_1$–$C_{30}$ alkyl and alkenyl radicals and aryl radicals, wherein at least one of the carbon atoms of the alkyl radicals, the alkenyl radicals and the aryl radicals is optionally replaced with a hetero atom chosen from N, S, O, and P;
- $R_{10}$ is chosen from linear and branched, optionally unsaturated alkylene groups optionally comprising at least one hetero atom chosen from N, O, S, and P; and
- $A^-$ is chosen from physiologically acceptable counterions.

12. The composition of claim 1, wherein Y is chosen from groups derived from ethylene glycol, diethylene glycol, and propylene glycol, and groups derived from polymers chosen from polyethers, sulfonated polyesters, and sulfonated polyamides.

13. The composition of claim 1, wherein the at least one cationic associative polyurethane has a number-average molecular mass ranging from 400 to 500,000.

14. The composition of claim 13, wherein the at least one cationic associative polyurethane has a number-average molecular mass ranging from 1000 to 400,000.

15. The composition of claim 14, wherein the at least one cationic associative polyurethane has a number-average molecular mass ranging from 1000 to 300,000.

16. The composition of claim 1, wherein the at least one cationic associative polyurethane is present in an amount ranging from 0.01% to 10% by weight relative to the total weight of the composition.

17. The composition of claim 16, wherein the at least one cationic associative polyurethane is present in an amount ranging from 0.1% to 5% by weight relative to the total weight of the composition.

18. The composition of claim 1, wherein the at least one oxidizing agent is chosen from hydrogen peroxide, compounds that release hydrogen peroxide by hydrolysis, chlorites, enzymatic systems that generate oxidizing species, and organic peroxides.

19. The composition of claim 18, wherein the compounds that release hydrogen peroxide by hydrolysis are chosen from urea peroxide and persalts.

20. The composition of claim 19, wherein the persalts are chosen from alkali metal and alkaline-earth metal persulfates and alkali metal and alkaline-earth metal perborates.

21. The composition of claim 18, wherein the enzymatic systems that generate oxidizing species are chosen from two-electron oxidoreductases combined with the donors thereof in the presence of air.

22. The composition of claim 21, wherein the two-electron oxidoreductases are chosen from uricases and the donor thereof is uric acid.

23. The composition of claim 18, wherein the at least one oxidizing agent is an aqueous hydrogen peroxide solution with a titer ranging from 1 to 40 volumes.

24. The composition of claim 18, wherein the concentration of the at least one oxidizing agent ranges from 0.1% to 25% by weight relative to the total weight of the composition.

25. The composition of claim 1, further comprising at least one direct dye.

26. The composition of claim 1, further comprising at least one additional polymer chosen from amphoteric and cationic polymers other than the at least one cationic associative polyurethane.

27. The composition of claim 26, wherein the cationic polymers are chosen from polyquaternary ammonium polymers comprising repeating units corresponding to formula (W):

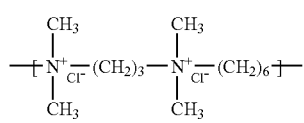

(W)

28. The composition of claim 26, wherein the cationic polymers are chosen from polyquaternary ammonium polymers comprising repeating units corresponding to formula (U):

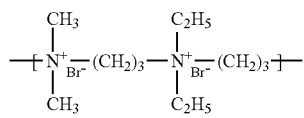

(U)

29. The composition of claim 26, wherein the amphoteric polymers are chosen from copolymers comprising at least monomeric units derived from acrylic acids and dimethyldiallylammonium salts.

30. The composition of claim 26, wherein the at least one additional polymer is present in an amount ranging from 0.01% to 10% by weight relative to the total weight of the composition.

31. The composition of claim 30, wherein the at least one additional polymer is present in an amount ranging from 0.05% to 5% by weight relative to the total weight of the composition.

32. The composition of claim 31, wherein the at least one additional polymer is present in an amount ranging from 0.1% to 3% by weight relative to the total weight of the composition.

33. The composition of claim 1, further comprising at least one surfactant chosen from anionic, cationic, nonionic, and amphoteric surfactants.

34. The composition of claim 33, wherein the at least one surfactant is present in an amount ranging from 0.01% to 40% by weight relative to the total weight of the composition.

35. The composition of claim 34, wherein the at least one surfactant is present in an amount ranging from 0.5% to 30% by weight relative to the total weight of the composition.

36. The composition of claim 1, further comprising at least one additional thickener.

37. The composition of claim 36, wherein the at least one additional thickener is chosen from cellulose derivatives, guar derivatives, gums of microbial origin, and synthetic thickeners.

38. The composition of claim 36, wherein the at least one additional thickener is present in an amount ranging from 0.05% to 10% by weight relative to the total weight of the composition.

39. The composition of claim 1, further comprising at least one basifying agent in an amount ranging from 0.05% to 30% by weight relative to the total weight of the composition.

40. The composition of claim 39, wherein the at least one basifying agent is chosen from aqueous ammonia, ammonium chloride, alkali metal and alkaline-earth metal carbonates, alkali metal and alkaline-earth metal silicates, alkali metal and alkaline-earth metal phosphates, alkanolamines and derivatives thereof, sodium hydroxide, potassium hydroxide and compounds of formula (XIX):

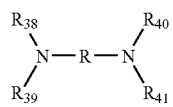

(XIX)

wherein R is chosen from propylene residues optionally substituted with at least one substituent chosen from hydroxyl groups and $C_1$–$C_4$ alkyl radicals; $R_{38}$, $R_{39}$, $R_{40}$, and $R_{41}$, which may be identical or different, are chosen from hydrogen, $C_1$–$C_4$ alkyl radicals, and $C_1$–$C_4$ hydroxyalkyl radicals.

41. The composition of claim 40, wherein the alkanolamines are chosen from monoethanolamine, diethanolamine and triethanolamine.

42. A ready-to-use composition for bleaching keratin fibers, comprising a mixture of at least one aqueous composition and at least one anhydrous composition comprising at least one oxidizing agent, wherein at least one of the anhydrous and aqueous compositions comprises at least one cationic associative polyurethane of formula (Ia):

$$R—X—(P)_n[L-(Y)_m]_r-L'-(P')_p—X'—R' \quad\quad (Ia)$$

wherein:
R and R', which may be identical or different, are chosen from hydrophobic groups and hydrogen;
X and X', which may be identical or different, are chosen from groups L" and groups comprising at least one amine functional group optionally bearing at least one hydrophobic group;

L, L', and L", which may be identical or different, are chosen from groups derived from diisocyanates;

P and P', which may be identical or different, are chosen from groups comprising at least one amine functional group optionally bearing at least one hydrophobic group;

Y is chosen from hydrophilic groups;

r is an integer ranging from 1 to 100; and n, m, and p, which may be identical or different, range from 0 to 1000; provided that the at least one cationic associative polyurethane comprises at least one amine functional group chosen from protonated and quaternized amine functional groups, and at least one hydrophobic group.

43. The composition of claim 42, wherein the mixture is made extemporaneously at the time of use.

44. The composition of claim 42, wherein the keratin fibers are human keratin fibers.

45. The composition of claim 44, wherein the human keratin fibers are hair.

46. The composition of claim 42, wherein the anhydrous composition is in pulverulent form.

47. The composition of claim 42, wherein the anhydrous composition comprises at least one additive chosen from mineral and organic fillers, binders, oils and waxes, polyalkylene glycols and polyalkylene glycol derivatives, lubricants, colorants, and matting agents.

48. The composition of claim 47, wherein the at least one additive is present in an amount ranging from 0 to 30% by weight relative to the total weight of the composition.

49. The composition of claim 1, wherein the medium suitable for bleaching is an aqueous medium.

50. The composition of claim 49, wherein the aqueous medium further comprises at least one organic solvent.

51. The composition of claim 50, wherein the concentration of the at least one organic solvent ranges from 0.5% to 20% by weight relative to the total weight of the composition.

52. The composition of claim 51, wherein the concentration of the at least one organic solvent ranges from 2% to 10% by weight relative to the total weight of the composition.

53. The composition of claim 49, wherein the aqueous medium comprises hydrogen peroxide.

54. The composition of claim 1, wherein the composition has a pH ranging from 4 to 12.

55. The composition of claim 54, wherein the composition has a pH ranging from 7 to 11.5.

56. The composition of claim 42, wherein the composition has a pH ranging from 4 to 12.

57. The composition of claim 56, wherein the composition has a pH ranging from 7 to 11.5.

58. The composition of claim 42, wherein the at least one cationic associative polyurethane is in an aqueous composition.

59. A process for bleaching keratin fibers, comprising applying to the keratin fibers a ready-to-use composition comprising, in a medium suitable for bleaching, at least one oxidizing agent and at least one cationic associative polyurethane, leaving the composition to act for an action time ranging from 1 to 60 minutes, rinsing the keratin fibers, optionally washing the keratin fibers with shampoo, and then rinsing the keratin fibers again and drying the keratin fibers, wherein the at least one cationic associative polyurethane is chosen from polyurethanes of formula (Ia):

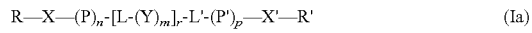

$$R—X—(P)_n\text{-}[L\text{-}(Y)_m]_r\text{-}L'\text{-}(P')_p—X'—R' \quad\quad (Ia)$$

wherein:

R and R', which may be identical or different, are chosen from hydrophobic groups and hydrogen;

X and X', which may be identical or different, are chosen from groups L" and groups comprising at least one amine functional group optionally bearing at least one hydrophobic group;

L, L', and L", which may be identical or different, are chosen from groups derived from diisocyanates;

P and P', which may be identical or different, are chosen from groups comprising at least one amine functional group optionally bearing at least one hydrophobic group;

Y is chosen from hydrophilic groups;

r is an integer ranging from 1 to 100; and n, m, and p, which may be identical or different, range from 0 to 1000; provided that the at least one cationic associative polyurethane comprises at least one amine functional group chosen from protonated and quaternized amine functional groups, and at least one hydrophobic group.

60. The process of claim 59, wherein the keratin fibers are human keratin fibers.

61. The process of claim 60, wherein the human keratin fibers are hair.

62. A multi-compartment device or kit for bleaching human keratin fibers, comprising a first compartment comprising at least one composition chosen from powder compositions and aqueous compositions, and a second compartment comprising an aqueous composition, wherein at least one of the two compartments comprises at least one oxidizing agent and at least one of the two compartments comprises at least one cationic associative polyurethane; and wherein the at least one cationic associative polyurethane is chosen from polyurethanes of formula (Ia):

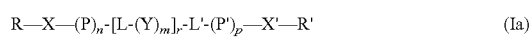

$$R—X—(P)_n\text{-}[L\text{-}(Y)_m]_r\text{-}L'\text{-}(P')_p—X'—R' \quad\quad (Ia)$$

wherein:

R and R', which may be identical or different, are chosen from hydrophobic groups and hydrogen;

X and X', which may be identical or different, are chosen from groups L" and groups comprising at least one amine functional group optionally bearing at least one hydrophobic group;

L, L', and L", which may be identical or different, are chosen from groups derived from diisocyanates;

P and P', which may be identical or different, are chosen from groups comprising at least one amine functional group optionally bearing at least one hydrophobic group;

Y is chosen from hydrophilic groups;

r is an integer ranging from 1 to 100; and n, m, and p, which may be identical or different, range from 0 to 1000;

provided that the at least one cationic associative polyurethane comprises at least one amine functional group chosen from protonated and quaternized amine functional groups, and at least one hydrophobic group.

63. The multi-compartment device or kit of claim 62, wherein the human keratin fibers are hair.

* * * * *